(12) United States Patent
Sellers

(10) Patent No.: US 9,370,648 B2
(45) Date of Patent: Jun. 21, 2016

(54) INJECTION MOLDED ADJUSTABLE SHAPE ABSCESS IRRIGATION DEVICE

(71) Applicant: MGS MFG. GROUP, INC., Germantown, WI (US)

(72) Inventor: Mark G. Sellers, Hartland, WI (US)

(73) Assignee: MGS Mfg. Group, Inc., Germantown, WI (US)

( * ) Notice: Subject to any disclaimer, the term of this patent is extended or adjusted under 35 U.S.C. 154(b) by 57 days.

(21) Appl. No.: 14/191,686

(22) Filed: Feb. 27, 2014

(65) Prior Publication Data

US 2014/0180259 A1     Jun. 26, 2014

Related U.S. Application Data

(62) Division of application No. 13/297,442, filed on Nov. 16, 2011, now Pat. No. 8,696,623.

(51) Int. Cl.
*A61M 27/00*     (2006.01)
*A61M 3/02*     (2006.01)

(52) U.S. Cl.
CPC .............. *A61M 27/00* (2013.01); *A61M 3/0283* (2013.01); *A61M 3/0291* (2013.01); *Y10T 29/49826* (2015.01)

(58) Field of Classification Search
CPC .. A61M 3/0291; A61M 3/0283; A61M 27/00
USPC ........................................................ 604/543
See application file for complete search history.

(56) References Cited

U.S. PATENT DOCUMENTS

| | | | | |
|---|---|---|---|---|
| 1,588,344 A | * | 6/1926 | Varney ................ | A61M 3/0291 604/107 |
| 1,665,790 A | * | 4/1928 | Novack ............... | A61M 3/0291 604/107 |
| 1,719,428 A | * | 7/1929 | Friedman ............ | A61M 3/0291 604/105 |
| 1,828,986 A | * | 10/1931 | Stevens ............... | A61M 3/0291 604/105 |
| 1,870,942 A | * | 8/1932 | Beatty ................. | A61M 3/0291 604/105 |
| 1,965,560 A | * | 7/1934 | Preston ............... | A61M 3/0291 604/107 |
| 1,972,428 A | * | 9/1934 | Richard .............. | A61M 3/0291 604/105 |

(Continued)

FOREIGN PATENT DOCUMENTS

| WO | 2005030035 A2 | 4/2005 |
|---|---|---|
| WO | 2005074520 A2 | 8/2005 |
| WO | 2009070686 A1 | 6/2009 |

*Primary Examiner* — Yogendra Gupta
*Assistant Examiner* — Emmanuel S Luk
(74) *Attorney, Agent, or Firm* — Boyle Fredrickson, S.C.

(57) ABSTRACT

An adjustable shape abscess irrigation device includes a first tube that is slidably associated with a second tube. The irrigation device includes a retainer that defines a variable shape diameter. The diameter of the retainer is selectively adjustable by the relative positioning of the first tube and the second tube such that, once placed relative to an abscess, the shape of the device can be manipulated to allow desired drainage of irrigation and abscess fluids beyond the confines of the abscess. Upon adequate drainage of the abscess, the cross-section shape of the retainer can be reduced to facilitate more comfortable and less detrimental removal of the device from the patient. Preferably, the irrigation device is formed via one or multi-shot injection molding and is formed of more than material.

7 Claims, 3 Drawing Sheets

(56) References Cited

U.S. PATENT DOCUMENTS

| | | | | |
|---|---|---|---|---|
| 2,556,783 | A * | 6/1951 | Wallace | A61B 17/22 604/105 |
| 2,649,092 | A * | 8/1953 | Wallace | A61M 25/04 604/105 |
| 3,108,595 | A * | 10/1963 | Overment | A61M 25/04 604/105 |
| 3,397,699 | A * | 8/1968 | Kohl | A61M 25/04 29/451 |
| 4,043,338 | A * | 8/1977 | Homm | A61M 31/00 604/105 |
| 4,521,938 | A * | 6/1985 | Kupcikevicius | A22C 11/0254 138/118.1 |
| 4,608,965 | A * | 9/1986 | Anspach, Jr. | A61B 17/0281 600/101 |
| 4,988,340 | A * | 1/1991 | Kitchin | A61M 27/00 604/543 |
| 5,112,310 | A | 5/1992 | Grobe | |
| 5,203,773 | A | 4/1993 | Green | |
| 5,232,440 | A | 8/1993 | Wilk | |
| 5,275,610 | A | 1/1994 | Eberbach | |
| 5,342,296 | A | 8/1994 | Person et al. | |
| 5,707,362 | A * | 1/1998 | Yoon | A61B 17/3417 604/164.03 |
| 5,882,340 | A | 3/1999 | Yoon | |
| 6,210,370 | B1 | 4/2001 | Chi-Sing et al. | |
| 6,361,563 | B2 * | 3/2002 | Terrill-Grisoni | 606/205 |
| 6,428,498 | B2 | 8/2002 | Uflacker | |
| 6,827,701 | B2 | 12/2004 | MacMahon et al. | |
| 6,942,641 | B2 | 9/2005 | Seddon | |
| 7,037,321 | B2 | 5/2006 | Sachdeva et al. | |
| 7,347,866 | B2 * | 3/2008 | Daignault | A61M 25/04 604/104 |
| 7,520,872 | B2 | 4/2009 | Biggie et al. | |
| 7,601,152 | B2 * | 10/2009 | Levy | A61B 17/7266 606/62 |
| 7,731,702 | B2 | 6/2010 | Bybordi et al. | |
| 7,938,842 | B1 * | 5/2011 | Chin | A61B 17/00008 604/104 |
| 8,007,508 | B2 * | 8/2011 | Cox | A61B 17/320016 606/198 |
| 8,052,711 | B2 * | 11/2011 | Hanse | A61N 1/057 606/198 |
| 8,696,623 | B2 * | 4/2014 | Sellers | A61M 3/0283 604/106 |
| 8,728,160 | B2 * | 5/2014 | Globerman | A61B 17/1637 623/17.11 |
| 2005/0004536 | A1 * | 1/2005 | Opie | A61B 17/00008 604/317 |
| 2005/0085769 | A1 | 4/2005 | MacMahon et al. | |
| 2009/0318898 | A1 | 12/2009 | Dein | |
| 2010/0145330 | A1 | 6/2010 | Badie | |
| 2013/0090183 | A1 * | 4/2013 | Hachiro | A63B 59/0033 473/300 |
| 2013/0123708 | A1 * | 5/2013 | Sellers | A61M 3/0291 604/177 |
| 2014/0041140 | A1 * | 2/2014 | Moskovich | A46B 5/02 15/143.1 |
| 2014/0165799 | A1 * | 6/2014 | Gauthier | B29C 45/0062 81/489 |
| 2015/0112314 | A1 * | 4/2015 | Gustaysson | B29C 45/261 604/544 |

\* cited by examiner

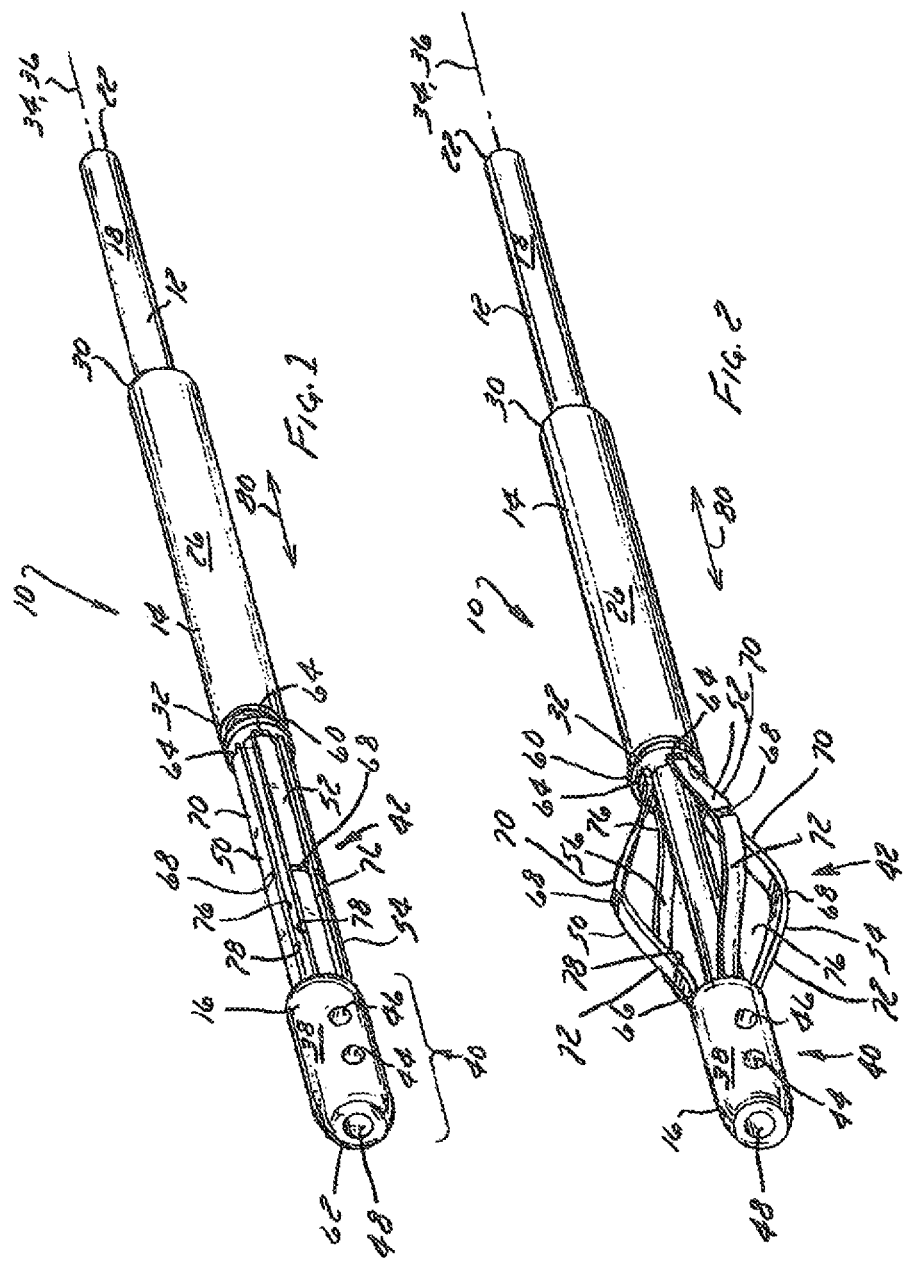

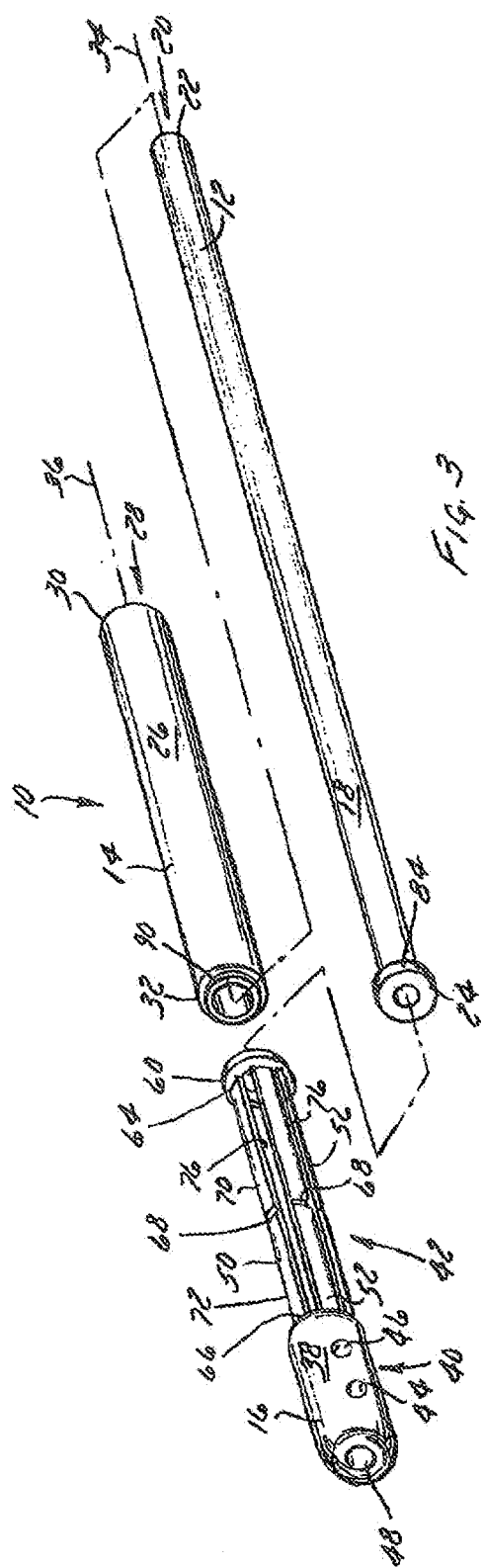
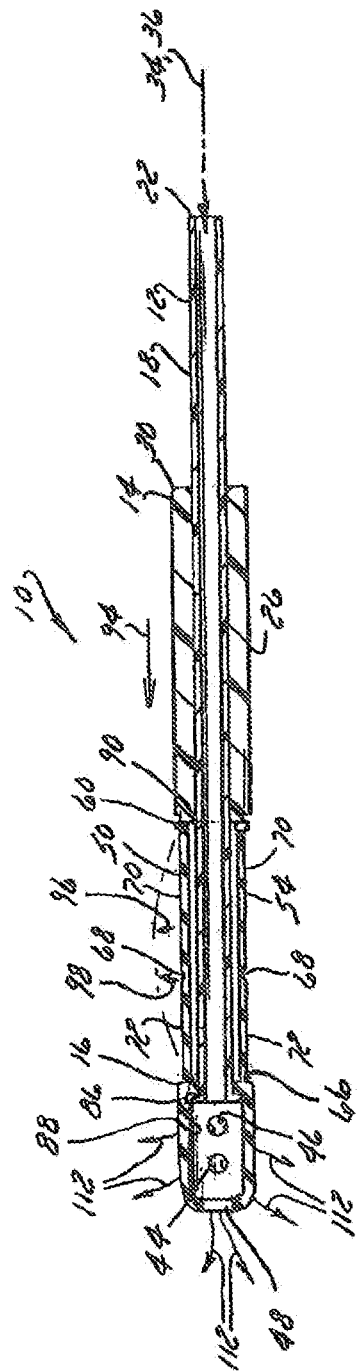
FIG. 3
FIG. 4

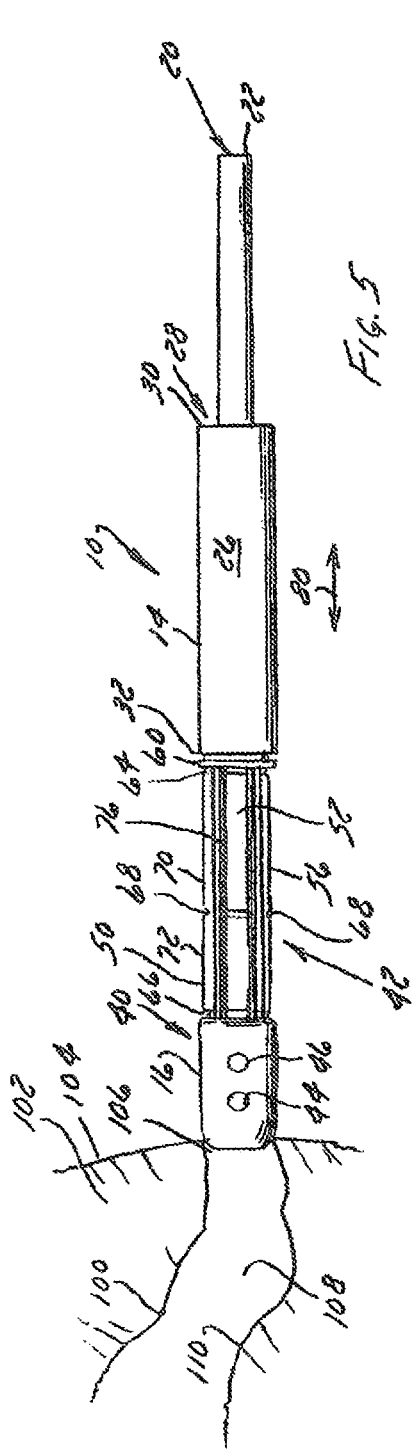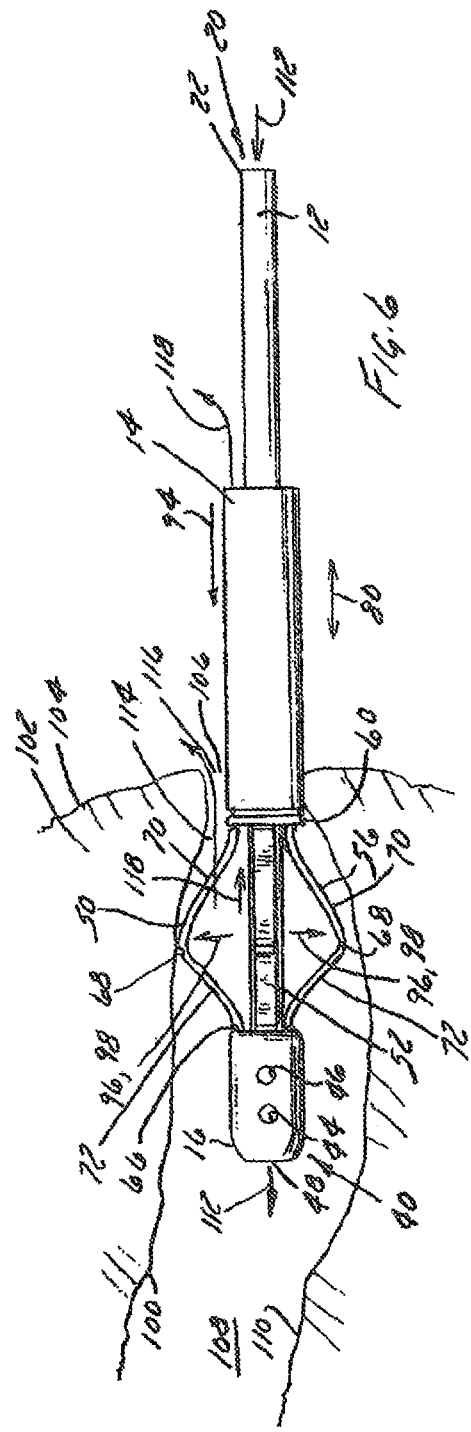

INJECTION MOLDED ADJUSTABLE SHAPE ABSCESS IRRIGATION DEVICE

CROSS REFERENCE TO RELATED APPLICATION

This application is a divisional application of allowed U.S. patent application Ser. No. 13/297,442 filed on Nov. 16, 2011 titled "Injection Molded Adjustable Shape Abscess Irrigation Device" and the disclosure of which is incorporated herein.

STATEMENT REGARDING FEDERALLY SPONSORED RESEARCH OR DEVELOPMENT

—

BACKGROUND OF THE INVENTION

The present invention relates to an abscess irrigation device, and in particular, to an injection molded abscess irrigation device that has an adjustable cross-sectional diameter and multiple fluid paths to effectuate desired irrigation and/or drainage of an abscess so as to reduce patient trauma attributable to changing the irrigation device during healing of the abscess.

Abscesses are localized infections of tissue marked by a collection of pus that is commonly surrounded by inflamed tissue. Abscesses may be found in any area of the body, but most abscesses which require more aggressive resolution are commonly found on the extremities, buttocks, breast, perirectal area, and/or associated with a hair follicle abnormality. Abscesses begin when a normal skin or tissue layer barrier is breached, and microorganisms and/or foreign matter or tissue invade underlying and/or adjacent tissues or tissue structures. Abscesses heal by drainage or removal of the foreign materials as well as loosened loculations within the abscess. Although smaller abscesses, in the range of smaller than approximately 5 mm in diameter or depth, can commonly be resolved with generally non-invasive methods, such as warm soaks to promote drainage, larger and/or deeper abscesses commonly require an incision, irrigation, and/or abridement to effectuate adequate drainage or irrigation of the abscess for healing of the surrounding tissue. Commonly, the increased inflammation, increased pus collection, and/or partial or complete walling off of the abscess cavity diminish the effectiveness of resolution via the conservative measures associated with warm soaks and/or the application of warm compresses.

As mentioned above, larger abscesses commonly appear on palpable skin. Deeper abscesses in very sensitive areas, such as supralevator, ischiorectal, perirectal positioned abscesses, commonly require a general anesthetic to obtain proper exposure of the abscess. Once incised, the abscess is irrigated and commonly left open to facilitate drainage. Alternatively, irrigation of the abscess can be effectuated with left-in-place irrigation devices. Commonly, such irrigation devices are provided in a number of different fixed shapes and sizes. After the necessary incision, a desired irrigation device is selected and placed in the abscess. The irrigation device is commonly held in place by suturing a portion of the incision snuggly about a portion of the irrigation device such that a portion of the irrigation device held within the void of the abscess by the surrounding anatomy of a patient and a second portion of the irrigation device extends beyond the epidermis of the patient for interaction with the various structures associated with irrigating the abscess.

Many such irrigation devices include a single fluid path that facilitates both the introduction of irrigation fluid into the abscess and the drainage of irrigated abscess fluid from the abscess. A fluid introduction tool, such as a syringe, cannula, or the like, is commonly connected to that portion of the irrigation device that extends beyond the patient. After the introduction of the irrigation fluid, the fluid introduction tool is removed from the irrigation device and the irrigation fluid and fluid associated with formation the abscess is allowed to drain through the same fluid path used to introduce the irrigation fluid. Subsequent flushing operations present the potential that previously flushed abscess fluid left within the fluid path is reintroduced into the abscess during subsequent irrigation operations. Accordingly, there is a need for an abscess irrigation tool that includes separate irrigation and fluid discharge paths.

During healing of the abscess during the irrigation sequence, it is commonly necessary to alter the position and/or shape of the irrigation device to allow better positioning of the irrigation device relative to the shape of the abscess and the surrounding tissue as well as the depth of the abscess and the space that is available based on the previous irrigation process. It is commonly desired and/or required to replace a first irrigation device with one or more subsequent irrigation device(s) that have different shapes and/or can better cooperate with the contours of the partially irrigated abscess. Commonly, as the abscess is repeatedly irrigated, the volume of the abscess shrinks thereby necessitating the use of sequentially smaller and/or irrigation devices having different shapes. Unfortunately, each replacement of a sequentially shaped irrigation device requires the repeated removal and replacement of the sutures associated with maintaining a desired positioning of the respective irrigation device. Accordingly, there is also a need for an abscess irrigation device whose size and position can be manipulated without undue interference and/or repeated manipulation of the anatomical and/or physiologic structures surrounding the abscess.

A number of currently available abscess irrigation devices commonly include a multiple part assembly that can include an adjustable spreader and/or an expandable bladder used to fully expose interior structure of the abscess and to better agitate abscess loculations for removal of the same. Unfortunately, such devices are not without further drawbacks. The multi-component and material assemblies commonly require disassembly to allow adequate cleaning for subsequent patient usage of the device. The various connection methodologies between the various connectable components of such abscess drainage devices are susceptible to fatigue and/or over pressurization failure and can subject a patient to undesired trauma associated with removal from the abscess after such separation.

To mitigate such detriments, others have provided drainage devices with oversized constructions and/or oversized connection methodologies. Unfortunately, such devices commonly require larger the desired incisions to facilitate cooperation of the drainage device with adjacent anatomy and are fairly uncomfortable for patient use. That is, when left in place for extended drainage durations, the various connections must be supported by the patient and are susceptible to unintended interaction with clothes or incidental contact with other rigid structures which can stress the sutures associated with maintaining the desired position of the in vivo portion of the drainage device. Particularly depending on the location of the abscess, such incidental contact can result in unnecessary pain and/or discomfort during the entire duration associated with drainage of the abscess. Accordingly, there is a further need for an abscess drainage device having a compact configuration when no irrigation device is engaged therewith.

SUMMARY OF THE INVENTION

The present invention provides an improved abscess irrigation device and method of forming the same that overcomes one or more of the drawbacks discussed above. The abscess irrigation device according to the present invention has an adjustable profile that provides improved drainage of the abscess and does so in a manner that is minimally invasive to a patient lifestyle when left engaged with an abscess for extended durations.

One aspect of the invention discloses an adjustable shape abscess irrigation device that includes a first tube that is slidably associated with a second tube. The irrigation device includes a retainer that defines a variable shape diameter. The diameter of the retainer is selectively adjustable by the relative positioning of the first tube and the second tube such that, once placed relative to an abscess, the shape of the device can be manipulated to allow desired drainage of irrigation and abscess fluids beyond the confines of the abscess. During drainage of the abscess, the cross-section shape of the retainer can be reduced or otherwise adjusted to facilitate an alternate orientation of the drainage device relative to the patient and/or more comfortable and less detrimental removal of the device from the patient upon complete drainage of the abscess. Preferably, the irrigation device is formed via one or multi-shot injection molding and is formed of more than material.

Another aspect of the invention discloses an abscess irrigation device having a tube with an elongate shape that extends between a first end and a second end. A fluid path is formed through the tube along the elongate shape. A second tube or sleeve is movably supported by the first tube and has a first sleeve end and a second sleeve end. A retainer is secured to the sleeve and the tube. The retainer includes at least two arms that extend in an outward radial direction relative to a longitudinal axis of the tube. A degree of extension of the arms from the longitudinal axis of the tubes is adjustably defined by a position of the sleeve relative to the tube.

Another aspect of the invention that is usable or combinable with one or more of the aspects above discloses a method of forming an anatomical drainage tool. A first tube is positioned concentrically with respect to a second tube. The first tube and the second tube are connected via a living hinge such that a relative positioning of the first tube and the second tube manipulates a radial diameter of the drainage tool via movement of the living hinge.

Another aspect of the invention that is usable with one or more of the above aspects discloses an abscess drainage tool having a first tube and a second tube that are slidably associated with one another. The tool includes a first fluid path formed through the first tube. The first tube and the second tube are connected by a retainer that has a variable diameter such that a relative orientation of the first tube and the second tube defines an instantaneous diameter of the retainer. A second fluid path is formed at least one of between the first tube and the second tube and between the second tube and adjacent anatomy such that fluid introduced into an abscess via one of the first fluid path and the second fluid path discharges from the abscess via the other of the first fluid path and the second fluid path.

In a preferred aspect, each of the first tube, second tube, and retainer are formed by a thermoplastic injection process. One or more the first tube, second tube, and retained may be formed during a single or multiple shot injection projection.

Preferably, the retainer is formed of a more pliable or flexible material than either of the first tube and the second tube. The first and second tube may be formed of the same material or can be formed of different materials such that one of the first tube and the second tube is more flexible than the other of the first tube and the second tube.

Preferably, the retainer includes a number of arms that extend in an outward radial direction from a longitudinal axis of the first tube and the second tube. Preferable, each flexible arm includes an intermediary living hinge, and a living hinge between the retainer and each of the first tube and the second tube. Preferably, a gap is formed between each arm and adjacent arms. The orientation or shape of the retainer is adjusted by the relative position of the first tube and the second tube. The relative orientation of the first tube and the second tube can be adjusted by a slidable and/or rotatable association between the first tube and the second tube.

Preferably, one or more of the first tube and the second tube include one or more vents that are shaped to direct an irrigation fluid into the confines of an abscess. Preferably, a first fluid path is used for the introduction of the irrigation fluid into the abscess and a second fluid path connected in series with the abscess and first fluid path is used to dispel or discharge the abscess irrigation fluid, abscess fluid, and abscess loculations from the abscess.

These various aspects, features, and advantages may apply to only some embodiments falling within the claims and thus do not define the scope of the invention.

BRIEF DESCRIPTION OF THE DRAWINGS

FIG. 1 is a perspective view side elevation view of an abscess irrigation device that is formed by an injection molding process and with a retainer in a first orientation according to the present invention;

FIG. 2 is a view similar to FIG. 1 of the abscess irrigation device shown in FIG. 1 with the retainer in a second orientation;

FIG. 3 is an exploded perspective view of the abscess irrigation device shown in FIG. 1;

FIG. 4 is a cross-sectional view of the abscess irrigation device shown in FIG. 1;

FIG. 5 is a side elevation view of the abscess irrigation device shown in FIG. 1 configured for initial engagement with an abscess; and FIG. 6 is a view similar to FIG. 5 with the abscess irrigation device configured for engagement with an abscess.

In describing the various preferred embodiments of the invention which are illustrated in the drawings, specific terminology is resorted to for the sake of clarity. However, it is not intended that the invention be limited to the specific terms so selected and it is to be understood that each specific term includes all technical equivalents which operate in a similar manner to accomplish a similar purpose. For example, the words connected, secured, attached or terms similar thereto are often used. They are not limited to direct connection unless otherwise specified but include connection through other elements where such connection is recognized as being equivalent by those skilled in the art.

DETAILED DESCRIPTION OF THE PREFERRED EMBODIMENT

Referring to FIGS. 1-3, an injection molded abscess irrigation device 10 according to the present invention includes a first tube 12, a second tube or sleeve 14, and a retainer 16 that is connected to tube 12 and sleeve 14. First tube 12 includes an elongate body 18 that defines a passage 20 that between a first end 22 to a second end 24 (FIG. 3) of tube 12. Sleeve 14 also includes an elongate body 26 that defines a passage 28 that extends from a first end 30 to a second end 32 of body 26.

Body 18 of tube 12 extends along a longitudinal axis, indicated by line 34, and is formed of a somewhat flexible material such that body 18 can be fairly easily deflected about axis 34 but is fairly rigid when subjected to forces generally aligned with longitudinal axis 34 of body 18. Body 26 of sleeve 14 also extends along a longitudinal axis, indicated by line 36, and is formed of a material that is preferably more rigid than the material of body 18 of tube 12 but also somewhat flexible so as to tolerate deflection about axis 36. Tube 12 and sleeve 14 are connected to one another by retainer 16 and configured so that sleeve 14 is translatable along the longitudinal length of tube 12.

Retainer 16 is defined by a body 38 and includes a head portion 40 and a deformable portion 42 that are integrally connected to one another. Head portion 40 includes one or more vents 44, 46, 48 that extend through body 38 of retainer 16. Vents 44, 46 are oriented radially with respect to axis 34, 36 whereas vent 48 is oriented in a distal end 62 of head portion 40 and generally aligned along axis 34, 36. As explained further below, it is appreciated that head portion 40 of retainer 16 could be provided with virtually any number and orientation of vents 44, 46, 48 to facilitate a desired introduction of flushing fluid into an abscess intended to be irrigated. It is further appreciated that alternate heads could be provided to provide alternate orientations of vents 44, 46, 48 to facilitate directional control of the introduction of flushing or irrigation fluid with respect to the particular geometry of a given abscess.

Deformable portion 42 of retainer 16 includes a number of flexible arms 50, 52, 54, 56 that each extend between head portion 40 and a collar 60 that is associated with or otherwise connected to sleeve 14. Retainer 16 is preferably constructed of a material that is more pliable and/or flexible than the material, of either tube 12 and/or sleeve 14. Each arm 50, 52, 54, 56 includes a first or sleeve living hinge 64, a second or tube living hinge 66 and a third or intermediary living hinge 68. Each intermediary hinge 68 is positioned along each of arms 50, 52, 54, 56 at a location that is between a sleeve hinge 64 and tube hinge 66. Each arm 50, 52, 54, 56 includes a first portion 70 that extends between first hinge 64 and intermediary hinge 68 and a second portion 72 that extends between second hinge 66 and intermediary hinge 68. A gap 76 is defined between adjacent edges 78 of adjacent arms 50, 52, 54, 56. As explained further below, gap 76 facilitates desired drainage of a respective abscess. It is further appreciated that although retainer 16 is shown as having four arms 50, 52, 54, and 56, retainer 16 could be provided with any number of flexible discrete arms that are movably associated with tube 12 and/or sleeve 14.

Arms 50, 52, 54, 56 are movable between a first orientation wherein arms 50, 52, 54, 56 closely overlie tube 12 (as shown in FIG. 1) and alternate orientations (such as that shown in FIG. 2), wherein arms 50, 52, 54, 50 stick out or extend in an outward radial direction relative to axis 34, 36 of tube 12 and sleeve 14, respectively. As explained further below, translation of sleeve 14, indicated by arrow 80, relative to tube 12 manipulates the orientation of arms 50, 52, 54, 56 in inward and outward radial directions relative to axis 34, 36 of tube 12 and sleeve 14 of abscess irrigation device 10 such that arms 50, 52, 54, 56 manipulate the cross sectional footprint of abscess irrigation device 10. It should be appreciated that the degree of longitudinal translation of sleeve 14 relative to tube 12 would define varying degrees of extension of arms 50, 52, 54, and 56 from axis 34, 36 and that device 10 thereby provides a retainer having an adjustable cross-sectional profile.

Referring to FIGS. 3 and 4, end 24 of tube 12 includes a lip 84 that passes through deformable portion 42 and arms 50, 52, 54, 56 of retainer 16 cooperates with a groove 86 (FIG. 4) formed on an interior surface 88 of head portion 40 of retainer 16. Arms 50, 52, 54, 56 extend longitudinally along and radially outboard along a portion of tube 12. Sleeve 14 includes a lip 90 that cooperates with collar 60 of retainer 16. Although tube 12, sleeve 14, and retainer 16 are shown as three separate elements (FIG. 3), it is appreciated that abscess drainage device 10 can be formed as a singular structure wherein tube 12, sleeve 14, and retainer 16 are inseparable from one another and yet movably associated as described further. It is further appreciated that one or more of tube 12, sleeve 14, and retainer 16 can be formed by any number of means including single or multiple step and single and/or multiple material injection molding processes.

As shown in FIG. 4, longitudinal translation of sleeve 14 relative to tube 12 in an expansion direction, indicated by arrow 94, causes the outward radial deflection, indicated by arrows 96, 98 of arm portions 70, 72 of each arm 50, 52, 54, 56. It is appreciated that translation 94 could be a truly linear translation along axis 34, 36 and/or include a rotational component such that sleeve 14 rotates about tube 12 so as to effectuate longitudinal translation 94. Regardless of the movement methodology, movement of one of tube 12 and/or sleeve 14 relative to the other of tube 12 and/or sleeve 14, changes the instantaneous shape and/or configuration of arms 50, 52, 54, and 56 of retainer 16 such that the shape of retainer 16, once positioned in vivo, can be manipulated from a location external to the patient. Preferably, an indexing or other securing mechanism is provided and maintains a desired orientation of sleeve 14 relative to tube 12 and thereby the orientation of shape of arms 50, 52, 54, 56 relative thereto. Such manipulation allows retainer 16 to achieve a desired orientation and/or shape with respect to axis 34, 36 and or the sidewalls associated with an abscess.

FIGS. 5 and 6 show alternate associations and orientations of abscess drainage device 10 with an exemplary patient 102 and exemplary abscess 100. Understandably, abscess 100 can be positioned virtually anywhere relative to the anatomy of a patient and have virtually any shape, size, and effective depth. Commonly, abscess 100 is internal to patient 102 and internal to the patient dermis or skin tissue 104. Creation of an incision or opening 106 allows the introduction of abscess drainage device 10 into a volume or cavity 108 defined by abscess 100. Abscess irrigation device 10 is introduced into cavity 108 such that arms 50, 52, 54, 56 can be positioned in cavity 108 and preferably slightly internal to skin tissue 104. It is appreciated that the location and orientation arms 50, 52, 54, and 56 may need to be periodically adjusted during treatment of abscess. When a desired depth is achieved, translation of sleeve 14 relative to tube 12, either radially or longitudinally, expands arms 50, 52, 54, 56 away from one another, away from the longitudinal axis 34, 36 of device 10, and into engagement with a tissue or wall surface 110 of abscess 100. Arms 50, 52, 54, 56 maintain a spatial relationship between abscess drainage device 10 and the surrounding tissue and/or abscess opening 106.

Second end 22 of tube 12 is preferably constructed to cooperate with a fluid delivery system, such as a syringe and/or a cannula, used to introduce a suitable abscess flushing or irrigation fluid through abscess drainage device 10 and into the cavity 108 associated with abscess 100. The irrigation fluid passes through passage 20 of tube 12 and is discharged into cavity 108 of abscess 100 via vents 44, 46, 48. Passage 20 and one or more of openings 44, 46, 48 define a first fluid path, indicated by arrow 112 for the exchange of fluid between cavity 108 of abscess 100 and atmosphere and/or locations external to cavity 108. It is appreciated that vents 44, 46, 48 can be constructed to provide directional control of the introduction of the irrigation fluid into cavity 108. Alternatively, head portion 40 of retainer 16 can have an external surface that is contoured to provide a direction component to the introduction of the irrigation fluid into cavity 108 to provide a desired fluid flushing of abscess 100.

Pus, irrigation fluid, abscess fluid and/or loculations are directed out of abscess cavity 108 via a fluid path that is in series with the first fluid path but only in fluid communication with the first fluid path 112 via fluid communication with cavity 108 of abscess 100. A second fluid path or abscess irrigation discharge path 114 can be formed between adjacent arms 50, 52, 54, and 56 and a separation 116 formed proximate incision opening 106 and the cooperation of the skin tissue 104 with the immediately adjacent portion of sleeve 14. The expanded or spread shape of arms 50, 52, 54, and 56 maintains a desired orientation of abscess irrigation device 10 relative to patient 102 but preferably maintains separation 116 therebetween such that irrigation fluid and abscess fluid and loculation material can be efficiently evacuated from abscess 100 during the irrigation process.

Alternatively, and/or in cooperation with separation 116, sleeve 14 can be maintained in an at least a partially spaced association with tube 12 such that irrigation and abscess fluid can vacate cavity 108 via such a spaced association between sleeve 14 with tube 12. As graphically shown in FIG. 6, such a fluid path 118 allows fluid associated with cavity 108 to pass between arms 50, 52, 54, and 56 and is directed between tube 12 and sleeve 14 such that the fluid is dispelled from abscess 100 proximate the relative location of end 30 of sleeve 14 over tube 12. It is further appreciated the internal and external surfaces of tube 12 and/or sleeve 14 can be fluted and/or provided with a helical shaped rib structure such to maintain the spacing associated with the passage of fluid from abscess 100 to atmosphere. It is further appreciated that the fluid flow directions associated with fluid paths 112, 114, 118 could equally be reversed in a manner wherein fluid is introduced into abscess 100 via one or more of paths 114, 118 and vacated therefrom via an alternate path of fluid paths 112, 114, 118. It is further appreciated that, tube 12 could also include one or more vents similar to vents 44, 46, 48 so as to provide irrigation performance along that portion of tube 12 that underlies arms 50, 52, 54, and 56 and/or sleeve 14.

Regardless of the irrigation flow direction, the adjustable variable diameter of retainer 16 as well as the externally adjustable nature of the cooperation of sleeve 14 and tube 12 allows retainer 16 to be repeatedly adjusted during the process of adequately draining or irrigating an abscess 100. The somewhat flexible nature of tube 12, sleeve 14, and retainer 16 allows abscess drainage device 10 to be positioned relative to an abscess and movably adjusted relative thereto without unduly interfering with patient lifestyle. That is, the reduced footprint of device 10 which extends beyond abscess 100 and the substantially self-supporting interaction of device 10 and the anatomy proximate abscess 100 provides an abscess irrigation device that is fairly unobtrusive when left in place to allow prolonged drainage of abscess 100 and can be quickly and conveniently reconfigured to manipulate the irrigation performance associated with use of device 10 until resolution of abscess 100 would dictate removal of the device from the patient.

Therefore, in accordance with one embodiment of the invention, an adjustable shape abscess irrigation device is disclosed that includes a first tube that is slidably associated with a second tube. The irrigation device includes a retainer that defines a variable shape diameter. The diameter of the retainer is selectively adjustable by the relative positioning of the first tube and the second tube such that, once placed relative to an abscess, the shape of the device can be manipulated to allow desired drainage of irrigation and abscess fluids beyond the confines of the abscess. Upon adequate drainage of the abscess, the cross-section shape of the retainer can be reduced to facilitate more comfortable and less detrimental removal of the device from the patient. Preferably, the irrigation device is formed via one or multi-shot injection molding and is formed of more than material.

Another embodiment of the invention that is usable with one or more of the aspects of the above embodiment includes an abscess irrigation device having a tube with an elongate shape that extends between a first end and a second end. A fluid path is formed through the tube along the elongate shape. A second tube or sleeve is movably supported by the first tube and has a first sleeve end and a second sleeve end. A retainer is secured to the sleeve and the tube. The retainer includes at least two arms that extend in an outward radial direction relative to a longitudinal axis of the tube. A degree of extension of the arms from the longitudinal axis of the tubes is adjustably defined by a position of the sleeve relative to the tube.

Another embodiment of the invention that is usable or combinable with one or more of the aspects of the above embodiment includes a method of forming an anatomical drainage tool. A first tube is positioned concentrically with respect to a second tube. The first tube and the second tube are connected via a living hinge such that a relative positioning of the first tube and the second tube manipulates a radial diameter of the drainage tool via movement of the living hinge.

Another embodiment of the invention that is usable with one or more of the aspects of the above embodiments includes an abscess drainage tool having a first tube and a second tube that are slidably associated with one another. The tool includes a first fluid path formed through the first tube. The first tube and the second tube are connected by a retainer that has a variable diameter such that a relative orientation of the first tube and the second tube defines an instantaneous diameter of the retainer. A second fluid path is formed at least one of between the first tube and the second tube and between the second tube and adjacent anatomy such that fluid introduced into an abscess via one of the first fluid path and the second fluid path discharges from the abscess via the other of the first fluid path and the second fluid path.

It is specifically intended that the present invention not be limited to the embodiments and illustrations contained herein, but include modified forms of those embodiments including portions of the embodiments and combinations of elements of different embodiments as come within the scope of the following claims

I claim:

1. A method of forming an anatomical drainage tool comprising:
   positioning a first tube concentrically with respect to a second tube;
   connecting the first tube to the second tube with a head portion and a deformable portion wherein the deformable portion includes a living hinge and the first tube and the second tube are connected such that a passage is formed between the first tube and second tube and a relative positioning of the first tube to the second tube manipulates a radial diameter of the drainage tool via movement of the living hinge of the deformable portion; and
   forming a plurality of vents in the head portion that are fluidly connected to a passage associated with the first tube and orienting the plurality of vents in the head portion such that at least one of the vents is directed in a longitudinal direction aligned with a longitudinal axis of the first tube and another of the plurality of vents is directed in a radial direction relative to the longitudinal axis of the first tube.

2. The method of claim 1 wherein manipulating the radial diameter of the drainage tool is performed by at least one of longitudinally translating and rotationally translating the second tube relative to the first tube.

3. The method of claim 1 further comprising forming the living hinge with a plurality of members that each extend in different radial directions from a longitudinal axis of the first tube.

4. The method of claim 1 further comprising forming the plurality of vents in the head portion such that a plurality of openings are directed in different radial directions relative to the longitudinal axis of the first tube.

5. The method of claim 1 further comprising forming the living hinge with a material that is more pliable than at least one of the first tube and the second tube.

6. The method of claim 1 further comprising injection molding the first tube, the second tube and the living hinge.

7. A method of forming an anatomical drainage tool comprising:
   positioning a first tube concentrically with respect to a second tube such that an interior of the first tube defines a first portion of an irrigation passage and a space between the first tube and the second tube defines a second portion of the irrigation passage and one end of the second portion of the irrigation passage is exposed to atmosphere when the anatomical drainage tool is associated with an abscess;
   connecting an end of the first tube to an end of the second tube with a head portion and a deformable portion such that positioning of the first tube relative to the second tube manipulates a radial diameter associated with the deformable portion via movement of the living hinge; and
   forming a plurality of vents in the head portion that are fluidly connected to the first portion of the irrigation passage associated with the first tube and orienting the plurality of vents in the head portion such that at least one of the plurality of vents is directed in a longitudinal direction aligned with a longitudinal axis of the first tube and at least two of the plurality of vents are directed in different radial directions relative to the longitudinal axis of the first tube such that the plurality of vents and any gaps between adjacent flexible arms associated with the deformable portion fluidly connect the first portion of the irrigation passage to the second portion of the irrigation passage.

* * * * *